(12) United States Patent
Sullivan et al.

(10) Patent No.: US 8,790,368 B2
(45) Date of Patent: Jul. 29, 2014

(54) TENODESIS IMPLANT

(75) Inventors: James J. Sullivan, Shrewsbury, MA (US); Richard M. Lunn, Kingston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 622 days.

(21) Appl. No.: 12/557,596

(22) Filed: Sep. 11, 2009

(65) Prior Publication Data

US 2010/0069958 A1 Mar. 18, 2010

Related U.S. Application Data

(60) Provisional application No. 61/097,885, filed on Sep. 18, 2008.

(51) Int. Cl.
*A61B 17/04* (2006.01)

(52) U.S. Cl.
USPC ............ 606/232; 606/325; 606/300; 606/75; 606/219

(58) Field of Classification Search
USPC ............ 606/232, 300, 325, 219, 75; 411/383
See application file for complete search history.

(56) References Cited

U.S. PATENT DOCUMENTS

| | | |
|---|---|---|
| 5,545,180 A | 8/1996 | Le et al. |
| 5,733,307 A | 3/1998 | Dinsdale |
| 5,766,250 A | 6/1998 | Chervitz et al. |
| 5,931,840 A * | 8/1999 | Goble et al. ................. 606/916 |
| 7,144,413 B2 * | 12/2006 | Wilford et al. ................ 606/232 |
| 7,572,283 B1 * | 8/2009 | Meridew ....................... 606/321 |
| 2002/0147463 A1 | 10/2002 | Martinek |
| 2002/0156476 A1 | 10/2002 | Wilford |
| 2002/0161401 A1 | 10/2002 | Steiner |
| 2006/0235413 A1 * | 10/2006 | Denham et al. ................. 606/72 |
| 2006/0253119 A1 | 11/2006 | Berberich et al. |
| 2006/0259076 A1 * | 11/2006 | Burkhart et al. .............. 606/228 |
| 2006/0276841 A1 | 12/2006 | Barbieri et al. |
| 2007/0156148 A1 | 7/2007 | Fanton et al. |
| 2008/0004659 A1 * | 1/2008 | Burkhart et al. .............. 606/232 |
| 2008/0009904 A1 * | 1/2008 | Bourque et al. .............. 606/232 |
| 2008/0275469 A1 * | 11/2008 | Fanton et al. ................. 606/139 |

FOREIGN PATENT DOCUMENTS

FR 2725126 A1 4/1996

* cited by examiner

*Primary Examiner* — Melanie Tyson
*Assistant Examiner* — Todd J Scherbel
(74) *Attorney, Agent, or Firm* — Norman F. Hainer, Jr.

(57) ABSTRACT

The present disclosure relates to a two-piece implant. The implant includes a first piece having at least two prongs and a protrusion located between the prongs and a second piece coupled to the first piece, wherein the second piece is configured to rotate relative to the first piece. A method of tissue repair is also disclosed.

12 Claims, 6 Drawing Sheets

TENODESIS IMPLANT

CROSS REFERENCE TO RELATED APPLICATIONS

This application claims priority to U.S. Patent Application No. 61/097,885 filed on Sep. 18, 2008, the disclosure of which is incorporated herein by reference in its entirety.

BACKGROUND

1. Technical Field

The present disclosure relates to soft tissue implants, and more specifically, an implant for use in tenodesis repair.

2. Related Art

Soft tissues, such as ligaments and tendons, can become torn or detached from bone. The tear or detachment may be repaired by inserting a surgical device, such as an anchor having an attached suture, into bone, and knotting the suture to secure the soft tissue to the bone. However, repairing the soft tissue in this manner can be technically demanding. In addition, the device docs not have the ability to solely manipulate the soft tissue, rather suture tying is required for primary fixation of the soft tissue.

SUMMARY

In one aspect, the present disclosure relates to a two-piece implant. The implant includes a first piece having at least two prongs and a protrusion located between the prongs; and a second piece coupled to the first piece, wherein the second piece is configured to rotate relative to the first piece. In an embodiment, the first piece includes a transverse opening located between the protrusion and a top surface of the first piece. In another embodiment, each of the at least two prongs include a radially-extending barb. In yet another embodiment, the top surface of the first piece includes a snap-fit feature for coupling of the second piece to the first piece. In a further embodiment, the second piece includes a bottom surface having an opening configured to engage the snap-fit feature and a top surface including a hole configured to engage a delivery device. In yet a further embodiment, the second piece includes threads on an outer surface of the second piece.

In another aspect, the present disclosure relates to a method of tissue repair including preparing a hole in a bone; placing a soft tissue over the hole; providing a two-piece implant including a first piece having at least two prongs and a protrusion located between the prongs and a second piece coupled to the first piece; and inserting the implant into the hole such that the implant advances the soft tissue into the hole.

In an embodiment, the soft tissue is advanced into the hole such that the protrusion of the first piece engages the soft tissue and the second piece is rotated relative to the first piece to advance the implant and the soft tissue into the hole. In another embodiment, the implant includes a transverse opening located between the protrusion and a top surface of the first piece. In yet another embodiment, at least one flexible member is disposed within the transverse opening. In a further embodiment, the method further includes placing ends of the at least one flexible member around the soft tissue before inserting the implant into the hole. In yet a further embodiment, the at least one flexible member is used to couple the implant to a delivery device. In an even further embodiment, each of the at least two prongs include at least one radially-extending barb, the barb engaging the bone when the implant is advanced into the hole, in an embodiment, the second piece includes threads on an outer surface of the second piece, the threads allowing for rotation of the second piece and advancement of the implant into the hole.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
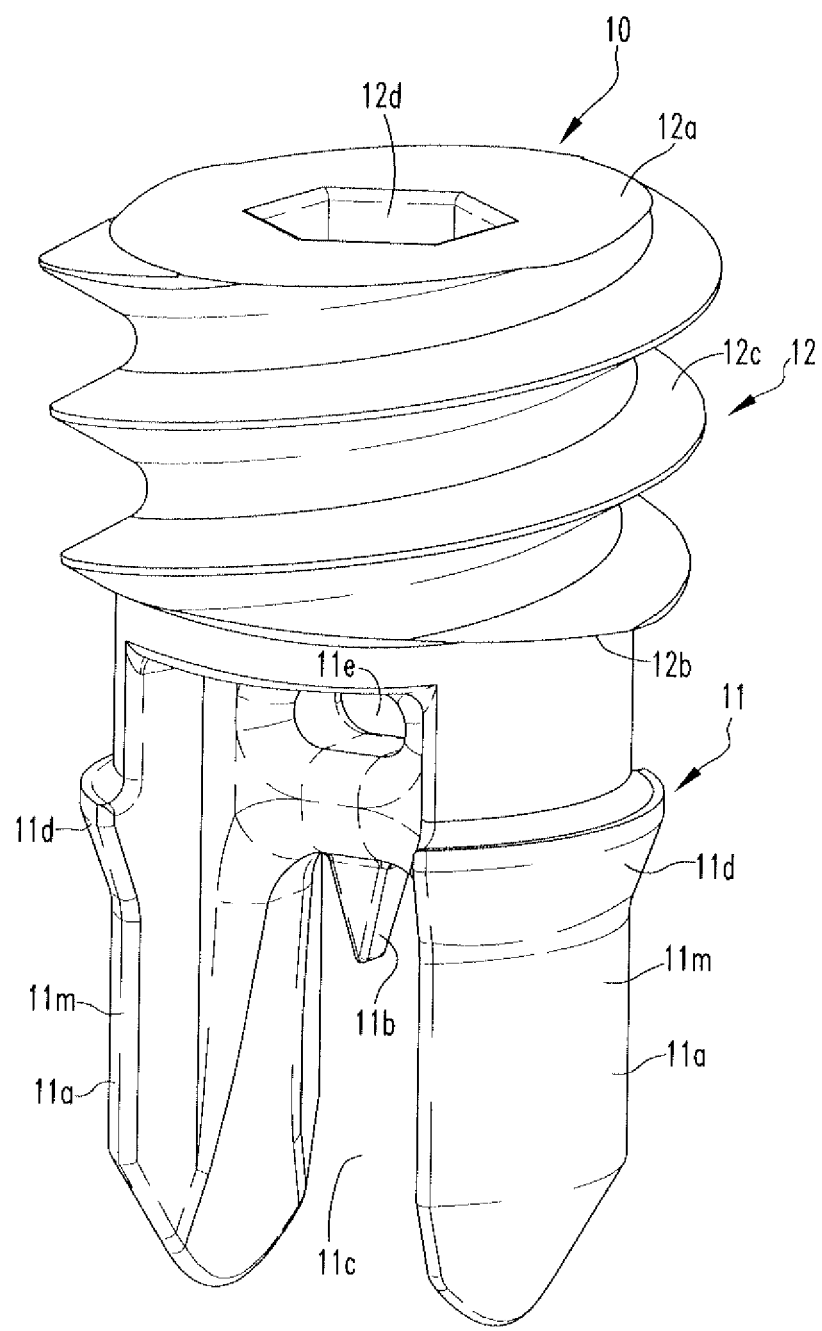
FIG. 1 shows a perspective view of the implant of the present disclosure.
Figure 2:
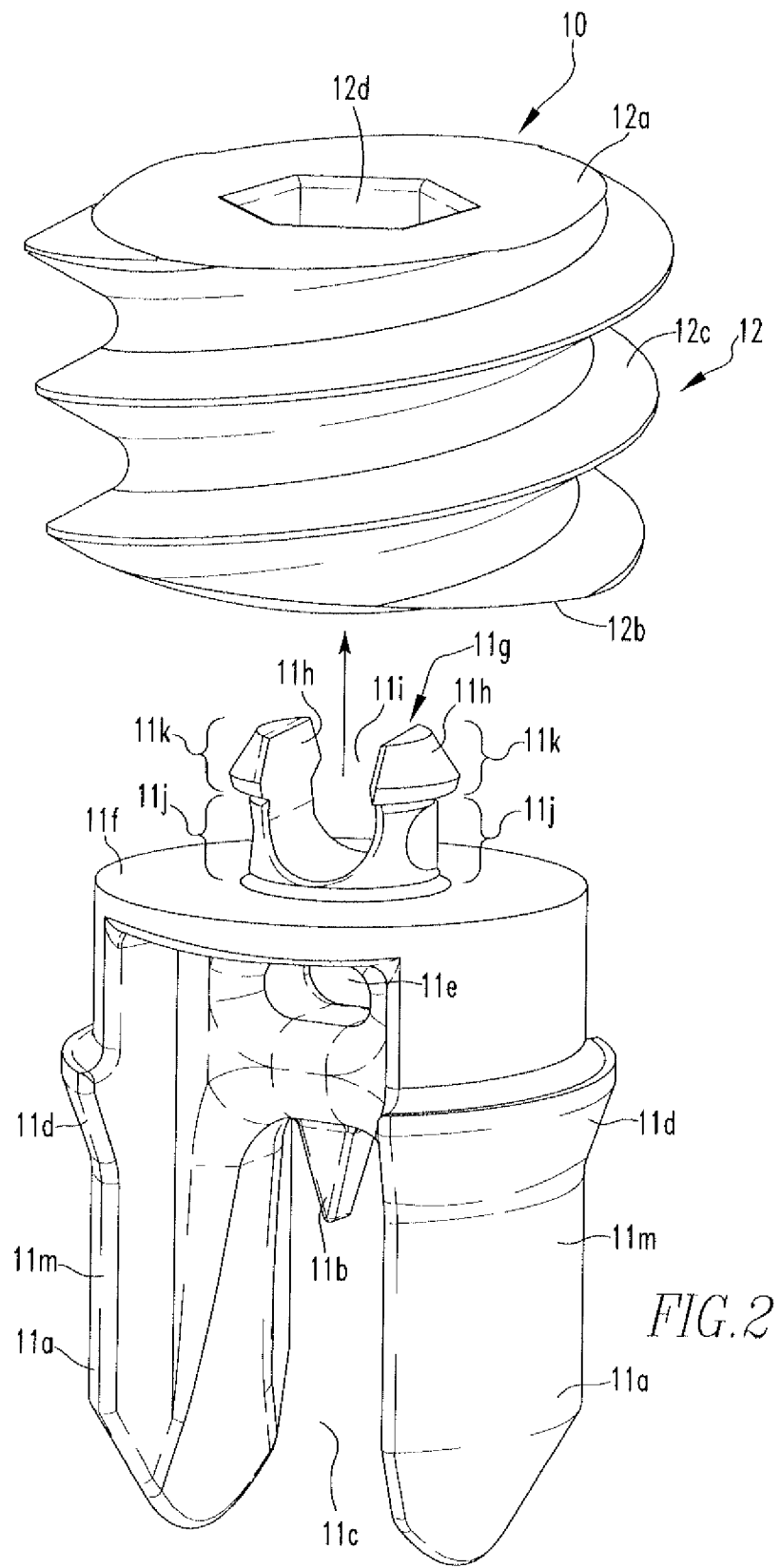
FIG. 2 shows an expanded view of the implant of FIG. 1.
Figure 3:
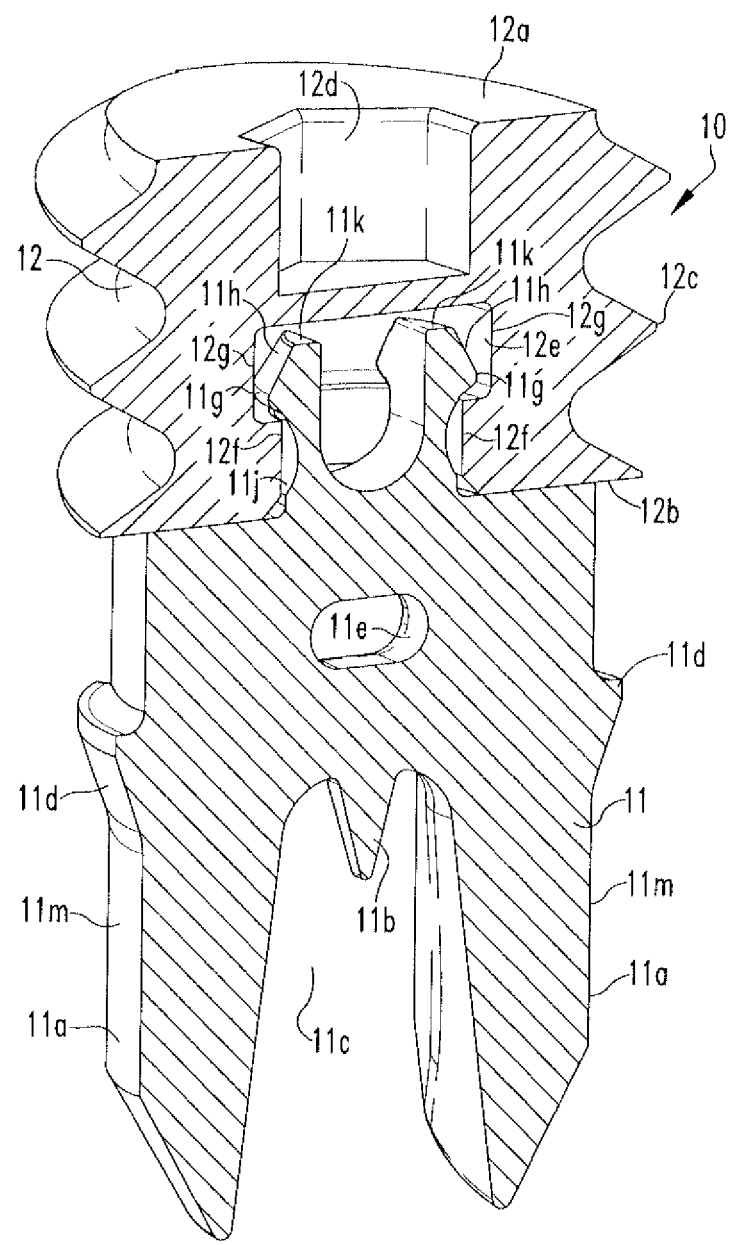
FIG. 3 shows a cross-sectional view of the implant of FIG. 1

FIGS. 1-3 show the two-piece implant 10 of the present disclosure. A first piece 11 includes two prongs 11a and a protrusion 11b located between the prongs 11a. A cavity 11c is located between the prongs 11a and, together with the protrusion 11b and the prongs 11a, capture a soft tissue for subsequent advancement into bone, as will be further described below. Each prong 11a includes an outer surface 11m having a radially-extending barb 11d located on the surface 11m. The barbs 11d reduce the possibility of removal of the implant 10 after advancement into bone, as will be further described below. More than one barb may be present on each prong 11a. A transverse opening 11c is located between the protrusion 11b and a top surface 11f of the first piece 11. The opening 11e allows for housing of a flexible member, such as a suture, the purpose of which will be further described below.

Located on the top surface 11f is a snap-fit feature 11g for coupling of a second piece 12 to the first piece 11. The feature 11g includes two arms 11h and a groove 11i located between the arms 11g. The arms 11g include bottom portions 11j and top portions 11k.

The second piece 12 includes a top surface 12a, bottom surface 12b, and a threaded outer surface 12c. As shown in FIG. 3, the top surface 12a includes a hole 12d configured for engagement with a delivery device, as will be further described below, and the bottom surface 12b includes an opening 12e configured for engagement with the snap-fit feature 11g. The hole 12d includes a hexagonal shape, but may be of another shape. The opening 12e includes a first portion 12f and a second portion 12g.

The second piece 12 is coupled to the first piece 11 such that the first portion 12f of the opening 12e is advanced over the top portions 11k of the arms 11g until the first portion 12f rests within the bottom portions 11j of the arms 11h and the top portions 11k of the arms 11h rests within the second portion 12g of the opening 12e, thereby allowing a snap-fit coupling between the first piece 11 and the second piece 12. The snap fit feature 11g also allows for rotation of the second piece 12 relative to the first piece 11, for purposes to be described later.

Figure 4A:
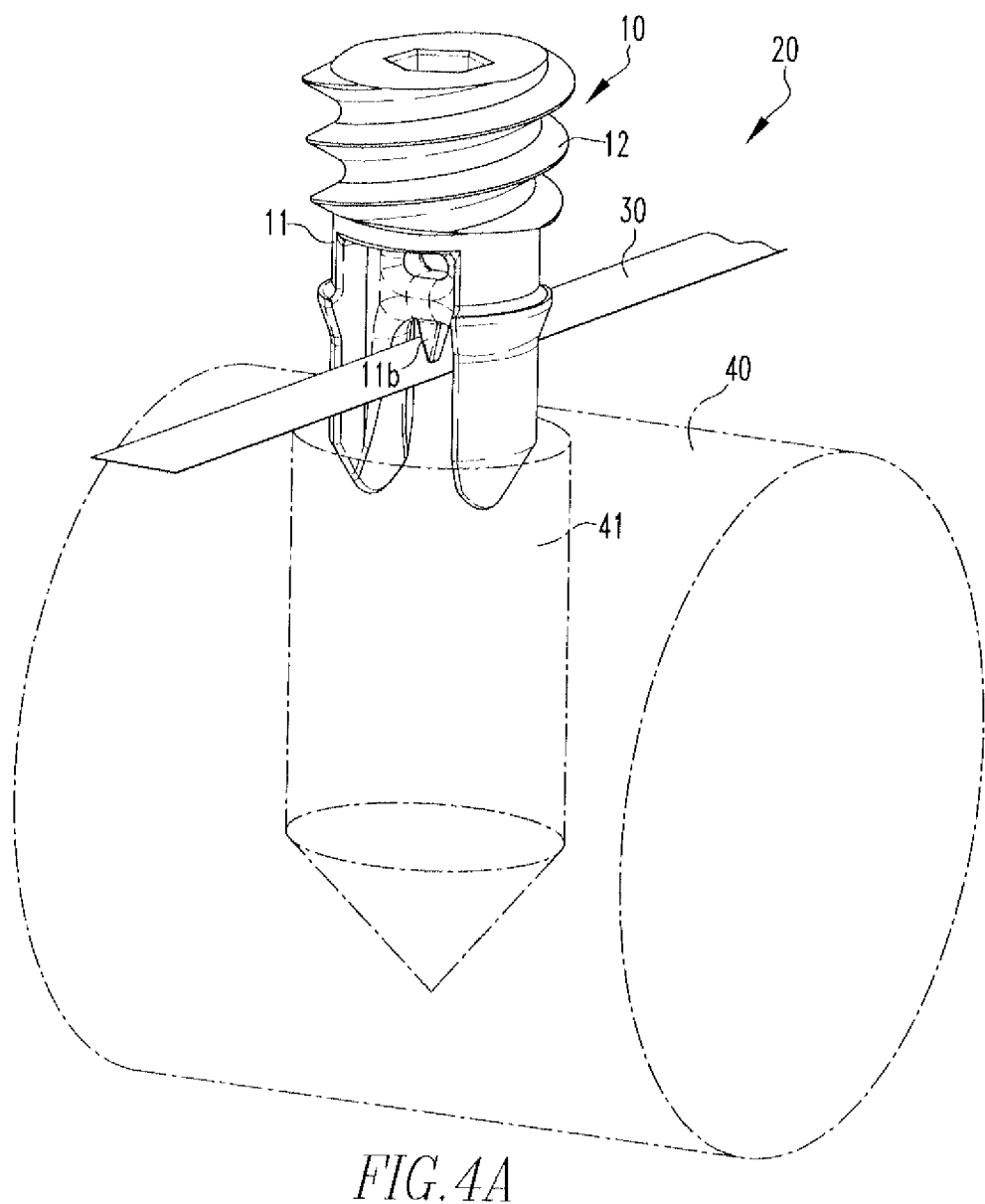
FIGS. 4A-4C show a method of tissue repair via use of the implant of FIG. 1.
Figure 4B:
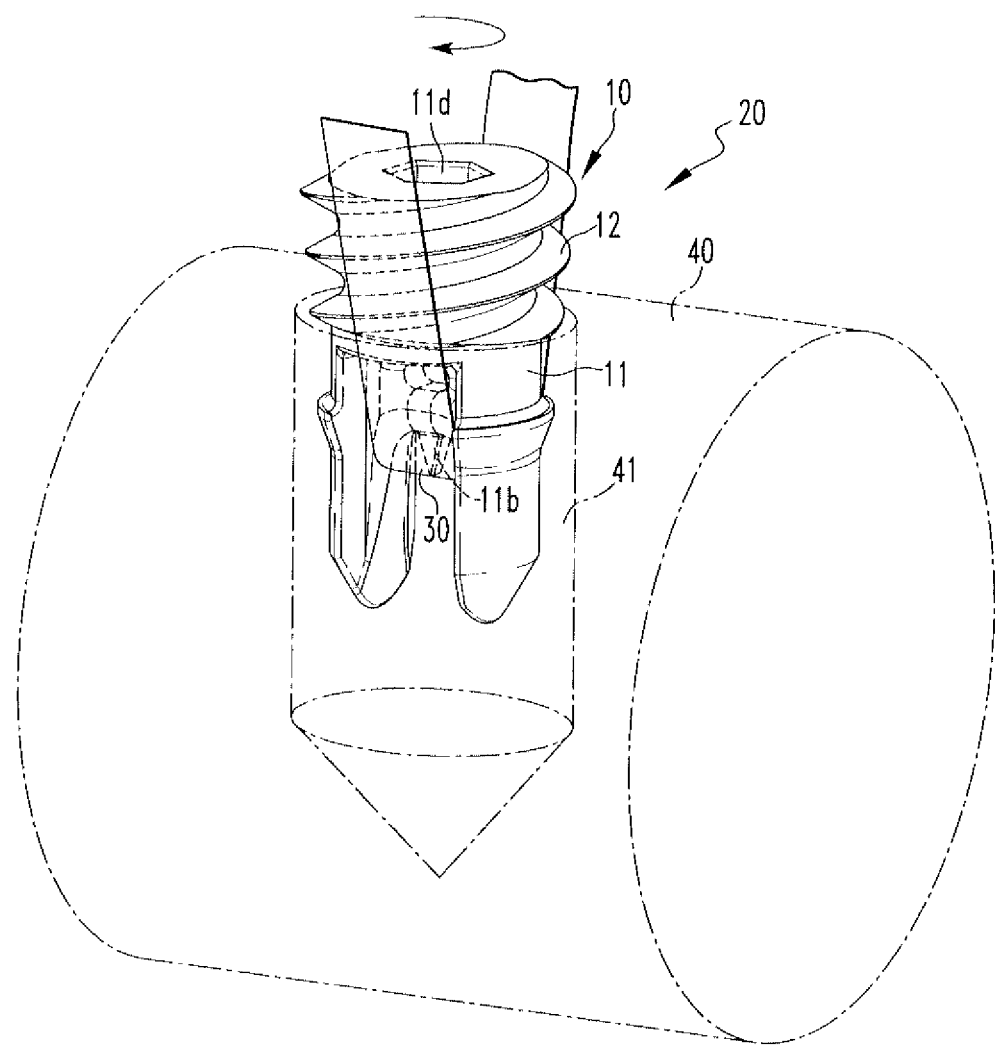
Figure 4C:
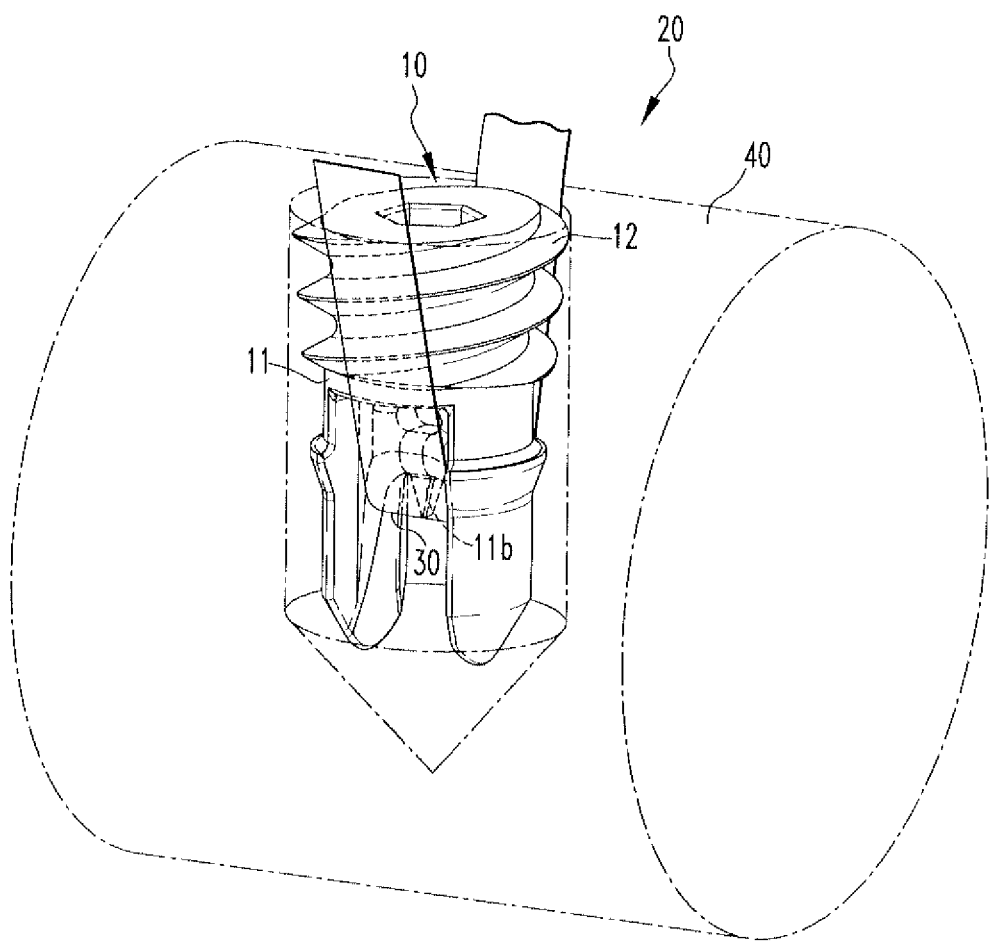

FIGS. 4A-4C show a method of tissue repair 20 via use of the two-piece implant 10 of the present disclosure. As shown in FIG. 4A, soft tissue 30 is placed over a previously prepared hole 41 in bone 40 and the implant 10 is used to initiate advancement of the soft tissue 30 into the bone 40 such that the soft tissue 30 is located within the cavity 11c and the protrusion 11b of the first piece 11 engages the soft tissue 30, as shown in FIG. 4A. Once the first piece 11 is advanced into the hole 41, the second piece 12 is rotated relative to the first piece 11 to further advance the implant 10 and the soft tissue 30 into the hole 41, as shown in FIGS. 4B-4C. For the purposes of this disclosure, advancement of the first piece 11 into the bone 40 is done via axial advancement and advancement of the second piece 12 into the bone 40 is done via rotary advancement.

A delivery device (not shown) that would allow both axial and rotary advancement is used. The delivery device may include a shaft having an outer surface configured to mate with the hole 12d, thereby allowing the device to rotate the second piece 12 relative to the first piece.

When the first piece 11 is advanced into bone 40, the radially-extending barbs 11d on the prongs 11a engage the bone 40, thereby increasing fixation of the implant 10 to bone 40. In addition, a flexible member (not shown), such as a suture, may be housed in the transverse opening 11c of the first piece 11 and may be used to further the coupling of the soft tissue 30 to the implant 10 prior to placement of the tissue 30 into the bone 40 or to further the coupling of the implant 10 to the delivery device. More than one flexible member may be used. Engagement of the soft tissue 30 by the protrusion 11b reduces the possibility of the soft tissue 30 from moving after the soft tissue 30 is advanced into the bone 40.

For the purposes of this disclosure, the first piece 11 is made from acetal and the second piece 12 is made from polyetheretherketone (PEEK). Both pieces 11,12 are made via an injection molding process. However, other materials and processes known to one of skill in the art may be used.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A two-piece implant comprising:
a first piece including at least two prongs, a protrusion located parallel to and between the prongs, and a snap-fit feature, wherein each of the at least two prongs includes a radially-extending barb, each of the barbs extending outwardly from an outer surface of the second piece; and
a second piece coupled to the first piece, the second piece including a bottom surface having an opening and a top surface including a hole, the opening and the hole separated from one another via a material separation, the material separation serving as a top surface of the opening and a bottom surface of the hole,
wherein the second piece is coupled to the first piece via the snap-fit feature and configured to rotate relative to the first piece, the snap-fit feature and the protrusion extending in opposite directions along the same longitudinal axis.

2. The implant of claim 1 wherein the first piece includes a transverse opening located between the protrusion and a top surface of the first piece.

3. The implant of claim 1 wherein the opening is configured to engage the snap-fit feature and the hole is configured to engage a delivery device.

4. The implant of claim 1 wherein the second piece includes threads on an outer surface of the second piece.

5. The implant of claim 1 wherein the snap-fit feature includes two arms and a groove located between the arms, each of the arms including a bottom portion and a top portion, the top portion having a larger diameter than the bottom portion.

6. The implant of claim 5 wherein the top portions of the arms are located in a second portion of the opening and a first portion of the opening is located adjacent the bottom portions of the arms.

7. The implant of claim 1 wherein the protrusion includes a pointed tip portion and extends axially from an outer surface of the second piece.

8. A two-piece implant comprising:
a first piece including at least two prongs, a protrusion located between the prongs, and a snap-fit feature, wherein each of the at least two prongs includes a radially-extending barb, each of the barbs extending outwardly from an outer surface of the second piece; and
a second piece coupled to the first piece, the second piece including a bottom surface having an opening and a top surface including a hole, wherein the opening and the hole are separated from each other via a material separation, the material separation serving as a top surface of the opening and a bottom surface of the hole, wherein the second piece is coupled to the first piece via the snap-fit feature and configured to rotate relative to the first piece, the snap-fit feature and the protrusion extending in opposite directions along the same longitudinal axis.

9. The implant of claim 8 wherein the protrusion includes a pointed tip portion and extends axially from an outer surface of the second piece.

10. The implant of claim 8 wherein the first piece includes a transverse opening located between the protrusion and a top surface of the first piece, the top surface including a snap-fit feature for coupling of the second piece to the first piece.

11. The implant of claim 10 wherein the snap-fit feature includes two arms and a groove located between the arms, each of the arms including a bottom portion and a top portion, the top portion having a larger diameter than the bottom portion.

12. The implant of claim 11 wherein the top portions of the arms are located in a second portion of the opening and a first portion of the opening is located adjacent the bottom portions of the arms.

* * * * *